(12) United States Patent
Lindfors et al.

(10) Patent No.: US 6,369,281 B1
(45) Date of Patent: Apr. 9, 2002

(54) PROCESS FOR THE PRODUCTION OF 2-BUTYL-2-ETHYL-1,3-PROPANEDIOL

(75) Inventors: Lars-Peter Lindfors, Espoo; Kalevi Heinola, Järvenpää; Kari Kulmala, Porvoo; Hannele Hakanpää-Laitinen, Helsinki; Lea Rintala, Porvoo; Lea Parkkinen, deceased, late of Porvoo, by Eero Joensuu, Tuija-Sisko Rainio, executors; Vesa-Matti Lehtinen, Porvoo, all of (FI)

(73) Assignee: Neste Oyj, Espoo (FI)

( * ) Notice: Subject to any disclaimer, the term of this patent is extended or adjusted under 35 U.S.C. 154(b) by 0 days.

(21) Appl. No.: 09/242,656

(22) PCT Filed: Aug. 19, 1997

(86) PCT No.: PCT/FI97/00484

§ 371 Date: May 30, 2000

§ 102(e) Date: May 30, 2000

(87) PCT Pub. No.: WO98/07675

PCT Pub. Date: Feb. 26, 1998

(30) Foreign Application Priority Data

Aug. 19, 1996 (FI) .................................................. 963243

(51) Int. Cl.⁷ .............................................. C07C 31/18
(52) U.S. Cl. ...................................... 568/852; 568/853
(58) Field of Search ................................. 568/852, 853

(56) References Cited

U.S. PATENT DOCUMENTS 2,413,803 A * 1/1947 Tribid et al. ................. 260/635
2,778,858 A * 1/1957 Meinhofer ................... 260/635

OTHER PUBLICATIONS

Charles I. Edwards, Chemical Abstracts, vol. 113, No. 9, Aug. 27, 1990.
Katsuhiko Tajima et al, Chemical Abstract, vol. 115, No. 23, Dec. 9, 1991.

* cited by examiner

Primary Examiner—Samuel Barts
Assistant Examiner—Elvis O. Price
(74) Attorney, Agent, or Firm—Birch Stewart Kolasch & Birch, LLP

(57) ABSTRACT

The present invention concerns a process for producing 2-butyl-2-ethyl-1,3-propanediol. According to the process, a reaction mixture is formed, containing 2-ethylhexanal and formaldehyde, into which an hydroxide compound is fed, whereby 2-ethylhexanal and formaldehyde are reacted to to produce 2-butyl-2-ethyl-1,3-propanediol. According to the invention, the hydroxide compound is incrementally fed into the reaction mixture. Preferably the hydroxide compound is fed at least at two input rates, in such a way that the heat production of the reaction between 2-ethylhexanal and formaldehyde immediately after each increase of the input rate of the hydroxide compound, is at least almost the same. The invention allows for the production of BEPD in a controlled and safe manner, with excellent yields.

23 Claims, 1 Drawing Sheet

PROCESS FOR THE PRODUCTION OF 2-BUTYL-2-ETHYL-1,3-PROPANEDIOL

This application is the national phase under 35 U.S.C. §371 of prior PCT International Application No. PCT/FI97/00484 which has an International filing date of Aug. 19, 1997 which designated the United States of America.

The present invention concerns a process according to the preamble of claim 1 for the production of 2-butyl-2-ethyl-1,3-propanediol.

According to said process, a reaction mixture is first formed, containing 2-ethylhexanal and formaldehyde, whereafter a suitable hydroxide compound is fed into the reaction mixture, whereby 2-ethylhexanal and formaldehyde react with each other, forming 2-butyl-2-ethyl1,3-propanediol.

The above compound, 2-butyl-2-ethyl-1,3-propanediol, in the following also abbreviated "BEPD", is a substance known per se, which is used for example in the manufacturing of polyester and in the paint industry as a component of powder paints. The excellent UV-protection provided by BEPD, and its very low water adsorption, are some of the advantages of the compound.

BEPD is manufactured from 2-ethylhexanal and formaldehyde in a single-step process through aldol addition, immediately followed by a Cannizzaro reaction. In the first reaction of the process, i.e. the aldol reaction, a basic alkali metal hydroxide or an alkaline earth metal hydroxide is usually used as a catalyst. In the second phase of the process, said hydroxide acts as a reactant, reacting with BEPD-aldol, an intermediate product of the aldol reaction. The hydroxide compound is fed to the reaction mixture in the form of an aqueous solution, whereby a two-phase product mixture is obtained when the reaction is complete. The organic phase of the mixture contains BEPD and the aqueous phase contains alkali metal or alkaline earth metal formates. The product reaction is very exothermic; the released heat of reaction is 200 kJ per mole of BEPD produced.

Known manufacturing processes of BEPD are described e.g. in U.S. Pat. Nos. 5,146,004, 5,177,267 and 5,235,118, in International Patent Application No. WO 93/02035, and in the JP Patent Applications 02062836 and 62129233.

Some considerable draw-backs are connected with the known methods. For example, the yields of BEPD are low, typically below 85%, and the production processes described in the prior art, have mostly been poorly reproducible on the basis of the information supplied in the publications. Low yields are at least partly due to the fact that heavy by-products are formed in the reaction mixture, under the influence of the heat released in the production process. They may amount to upto 20%, and thus significantly decrease the yield of BEPD. On the other hand, the reaction times must be kept quite long, from an economic point of view, because of the violent heat production of the exothermic reaction, which otherwise easily may push the reaction beyond control.

For the sake of completeness, it should be mentioned that there are methods known in the art for preparing which 2,2-disubstituted 1,3-propanediols from the aldehyde by aldol condensation and a subsequent Cannizzaro reaction, in which the alkali is fed into the reaction mixture at two feed rates. Reference is made to the following publications: DE Patent Specification No. 1,057,083, U.S. Pat. No. 2,778,858 and Chemical Abstracts 115 (1991) 255628w. In these technical solutions there is an interval between the feeds and the heat production is also rather uncontrolled.

In our earlier invention, described for example in the International Patent Application No. WO 95//00464, a solution has been disclosed for the production of BEPD using a phase shift catalyst. This process, in which a formaline solution, almost free from methanol, or instead of a solution, solid paraformaldehyde, is used, allows for very good yields (up to over 92%) and low reaction times.

It is an object of the present invention to eliminate the draw-backs of the known technique and to achieve a new process for the production of BEPD with high yield and as pure a product as possible, starting from 2-ethylhexanal and a formaline solution containing methanol, and using an alkali metal or alkaline earth metal hydroxide or similar hydroxide compound as catalyst and reactant.

The present invention is based on the concept of feeding the hydroxide compound continuously and incrementally into the reaction mixture of 2-ethylhexanal and formaldehyde in order to control the heat production of the reaction. Thereby the feeding rate of the hydroxide compound is not constant throughout the reaction, but it is increased stepwise or continuously. Thus, in the beginning of the reaction, when the production of reaction heat is at its highest, the hydroxide compound is fed into the reactor at a rate smaller than that used in the prior art, after which the input is increased as the reaction proceeds.

More specifically, the process according to the invention is mainly characterized by what is stated in the characterizing part of claim 1.

The invention provides considerable advantages. Thus, for instance, the production of BEPD is fully controlled, safe, and gives high yields. Furthermore, the formation of byproducts may be minimized. As shown in the examples below, less than 5% by-products are formed in the conditions according to the invention. The use of the cooling capacity of the production equipment can be made more efficient by the invention. Compared to the above mentioned publications, DE Patent Specification No. 1,057,083, U.S. Pat. No. 2,778,858 and Chemical Abstracts 115 (1991) 255628w, the invention avoids uncontrolled temperature variations and the reaction temperature can be adjusted with an accuracy of one degree even on a production scale basis. Furthermore, by proper control of the thermochemistry it is possible considerably to shorten the reaction time and no additives are needed for homogenization of the reaction mixture.

In the following, the invention is disclosed through a more detailed description and some working examples.

The production is carried out as a batch, semi-batch or continuous process. The latter two modes are considered the most advantageous. The examples below describe the implementation of the process in a semi-batch reactor equipped with efficient mixing, whereby the calculated amount of 2-ethylhexanal and formaldehyde is first fed into the reactor, forming the reaction mixture, whereafter a suitable hydroxide compound is added to the reaction mixture. Hydroxide is continuously brought into to blend in order to control the heat of reaction. This will also appear from the attached drawing which depicts the generation of reaction heat as a function of the reaction time. The reaction mixture is mixed throughout the reaction. After the reaction, the two-phase reaction mixture is allowed to separate in phases. The organic phase of the mixture contains BEPD, possibly together with some organic impurities. The water phase contains alkali metal or alkaline earth metal salts. The reaction mixture can be separated and washed in two alternative ways, described in more detail below.

The incremental feed of the hydroxide compound can, according to the invention, be accomplished either continuously or in steps. In the latter case, the hydroxide compound is fed at, at least, two different rates, so that the heat production of the reaction between 2-ethylhexanal and formaldehyde, is at least approximately equally large after each increase of feeding rate. The hydroxide compound can be fed into the reaction mixture also at three or more different feeding rates, whereby the new rate is always about 10 to 100%, preferably about 20 to 80%, larger than the previous rate.

In an alternative embodiment, the feed is continuous and the feeding rate of the hydroxide compound is continuously increased. In both embodiments, the amount of hydroxide compound fed into the reaction per unit time is increased at least by a factor of 1.5 or 2 during the reaction.

The amount of hydroxide compound to be fed depends on the amount of 2-ethylhexanal. According to the invention, it has been found preferable to keep the molar ratio of the total input of hydroxide compound (i.e. the total amount of hydroxide fed into the reaction mixture) and 2-ethylhexanal at a value, which is larger than 1, preferably about 1.2 to 1.5.

In the invention, 2-ethylhexanal is preferably used in the form of as pure as possible a solution (purity preferably >90%, in particular over 95%). Formaldehyde and the hydroxide compound are used in the form of aqueous solutions, preferably as concentrated aqueous solutions, whereby the concentration of formaldehyde in the aqueous solution is 30 to 50 weight-%. This aqueous solution contains most preferably 2 to 20 wt-% some lower alcohol, such as methanol. Methanol or a corresponding alcohol stabilizes the formaline solution and prevents dimerizing of formaldehyde. The hydroxide compound is most preferably used in the form of as strong as possible an aqueous solution or suspension, the concentration of e.g. sodium hydroxide being preferably over 40%, in particular over 45%. In addition to sodium hydroxide, other alkali metal hydroxides may be used as hydroxide compounds, for instance potassium or lithium hydroxide, and alkaline earth metal hydroxides, such as calcium and magnesium hydroxide. The molar ratio of formaldehyde to 2-ethylhexanal is about 2.1 to 5, preferably 2.3 to 3.0, and the corresponding molar ratio with respect to the hydroxide compound is 1.5 to 3, preferably about 1.9 to 2.1.

It should be mentioned, that besides the formaline solution, paraformaldehyde can also be used, which decomposes in the reaction mixture, forming formaldehyde.

The temperature of the reaction is kept at 40 to 80° C., preferably 50 to 70° C., at least essentially during the reaction. At lower temperatures the reaction phases of the process may constitute a safety risk, because of the reaction kinetics. The reaction time varies depending on the amounts of reactants, on the reaction temperature, and in particular on the amount of hydroxide compound feed, but is typically about 1 to 24 hours, preferably about 4 to 12 hours. In the examples described below, 6 hour reaction times were used. The 2-ethylhexanal used as feedstock reacts usually completely within 4 hours; and t he concentration of the BEPD-aldol that is formed as an intermediate product is at its highest (ca 50%) after about three hours.

After the reaction is completed, the yield of BEPD calculated from ethylhexanal is over 90%. The reaction mixture is removed from the reactor, the blend is washed, and BEPD is separated from the organic phase by distillation at reduced pressure. By washing the BEPD the alkali or earth alkaline salts, formed in the reaction, are principally separated from the product. Heavy organic impurities are removed from BEPD in connection with the distillation.

BEPD may be purified by a method known per se, for instance:

The reaction mixture is first neutralized with (concentrated) sulphuric acid, setting the pH value to 5–7. After this, the reaction mixture is mixed for 1–60 minutes, typically ca 5–30 minutes, after which the phases are allowed to separate, the aqueous phase is removed and the organic phase is washed twice during mixing. The first washing is performed with water containing sodium hydroxide, which increases the pH value to ca 12–14; the second washing is done using acidified water (sulphuric acid), to make the pH value at least about neutral (ca 6 to 7). After each washing turn the phases are allowed to separate and the aqueous phase is removed. The objective of the alkaline washing is to separate the acid fractions, which may disturb the distillation of BEPD and cause problems with corrosion. The raw BEPD product obtained is distilled at low pressure at 120–140° C. (9 mmHg). Salts can be recovered from the aqueous phase, separated form the product blend, and further processed.

In an alternative washing method, preferred according to the invention, the reaction mixture is not neutralized with sulphuric acid after the completion of the catalyst feed. Instead, the produced blend is allowed to separate into phases, and the aqueous phase is removed from the reactor as soon as possible after the completion of the catalyst input. After this the produce is washed in the reactor in one or two steps with pure water. The mass of the washing water in relation to the mass of the organic phase is 0.2 to 1.0, preferably 0.4 to 0.5, in the first step, and 0.2 to 1.0, preferably 0.2–0.4 in the second step, if a two-step washing is used. In the case of single-step wash, the corresponding ratio is 0.5 to 0.9. In the purification of the product, a washing efficiency of up to 94 to 96% is attained, including the concentration of the sodium (or corresponding alkali metal or alkaline earth metal) ion. If necessary, the pH value is controlled in connection with the latter washing, as described above. The produced raw BEPD product is distilled as described above.

The washing method disclosed above has some important advantages compared to the traditional method of washing. For instance, the number of processing phases is smaller, because no addition of sulphuric acid is needed. The product phase may be washed with pure water instead of with lye containing water, because no shifting of pH back to the neutral range is needed. The costs of raw material are lower, because no sulphuric acid or lye is needed in connection with the washing. The washing efficiency is better, because the ion content of the product is not increased during the washing. For the same reason, the ionic content of the process and washing waters are lower, leading to less environmental loading. In the distillation of the product, acid fractions can be avoided (meaning less problems with corrosion). If necessary, the washing of the product may be done in one step.

The following non-limiting working examples illustrate the invention.

BRIEF DESCRIPTION OF DRAWINGS

The calorimetergram of Example 1 is shown in FIG. 1.

EXAMPLE 1

Figure 1:
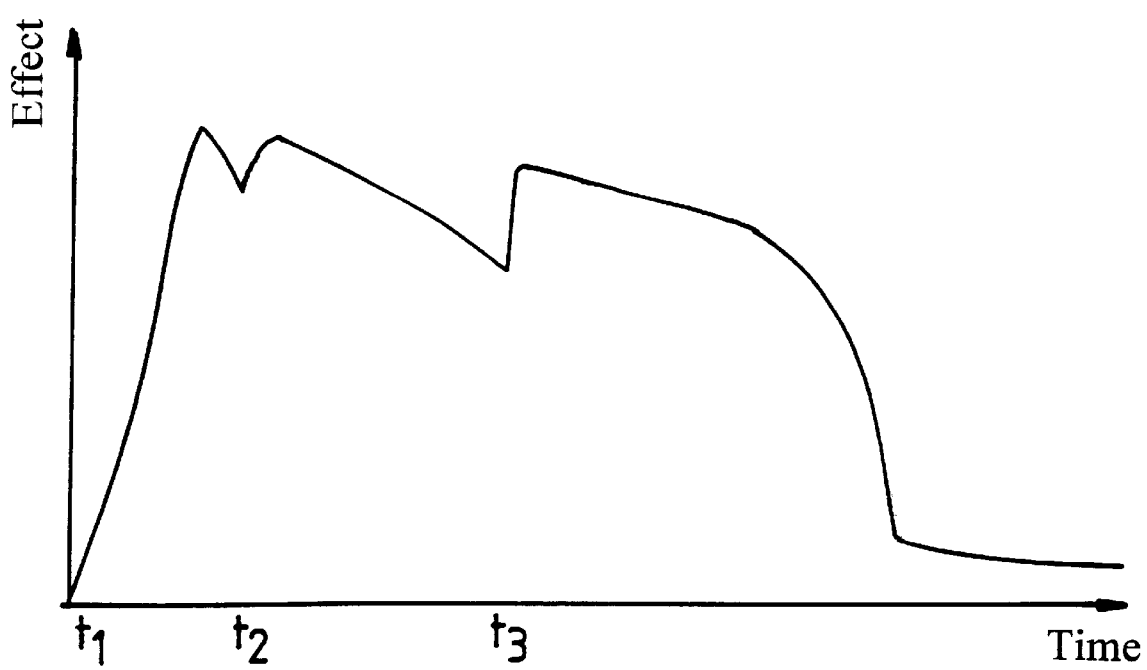

BEPD was prepared by a semi-batch process out of 2-ethylhexanal (2-EH), having a purity of over 90 weight-%, and formaline. The concentration of the formaline aqueous solution was 37 weight-% HCHO and it contained 10 weight-% $CH_3OH$. First, 1207 g (9.225 moles) of 2-EH and 1911 g (23.546 moles) of HCHO were fed into the reactor to make up the reaction mixture, after which 927 g (11.125 moles) in total of sodium hydroxide was fed into the reaction mixture. The concentration of the sodium hydroxide aqueous solution was 48 weight-%, and it was fed for 6 hours at three input rates, namely 93 g/h (1.1161 moles per hour) during the first hour of the reaction (beginning at time $T_1$), 135 g/h of NaOH (1.6201 moles/h; beginning at time $T_2$) during the following two hours and, finally, 188 g/h (2.2562 moles/h; beginning at time $T_3$) during the third to the 6th hour.

After the reaction, the product blend was neutralized with strong (97 w-%) sulphuric acid. After the input of sulphuric acid, the aqueous phase was separated from the organic phase, which contained BEPD. The content of BEPD was then 94.6 weight-%. The pH value of the organic phase was made alkaline by washing with NaOH, which removes the acid fraction. Finally, the pH value of the organic phase was set to 6.5–7, by sulphuric acid addition, after which the organic phase was distilled at underpressure.

EXAMPLE 2

The process described in Example 1 was repeated in the laboratory reactor, using formalin of 46 weight-%, containing 5 weight-% methanol. The amount of 2-ethylhexanal was 1215 g and the amount of formalin was 1543.5 g. The input rates of the sodium hydroxide solution (48 weight-%) were: 0–1 h: 95.18 g/h (1.1422 moles/h), 1–3 h: 138.03 g/h (1.6563 moles/h) and 3–6 h: 192.25 g/h (2.307 moles/h), whereby the total amount of sodium hydroxide was 948 g. The ratio of formaldehyde to 2-ethylhexanal was 2.5 and the ratio of sodium hydroxide to 2-ethylhexanal was 1.2. The content of BEPD was then 95.6 weight-%.

The product blend was washed in the manner described in Example 1.

For comparison, BEPD was produced according to known techniqe, by feeding 170 g sodium hydroxide at constant rate for two hours into a reactor containing 218 g 2-EH and 218 g formaldehyde. The BEPD concentration obtained was 78.27 weight-% and biproducts were present at 18.84 weight-%.

What is claimed is:

1. A process for producing 2-butyl-2-ethyl-1,3-propanediol, comprising feeding a hydroxide compound into a reaction mixture containing 2-ethylhexanal and formaldehyde wherein said hydroxide compound is fed into the reaction mixture continuously and incrementally to produce 2-butyl-2-ethyl-1,3-propanediol such that the reaction mixture is maintained in two phases, an organic phase and an aqueous phase throughout the entire production process.

2. The process according to claim 1, wherein the input rate of the hydroxide compound is increased stepwise during the reaction of 2-ethylhexanal and formaldehyde.

3. The process according to claim 2, wherein the hydroxide compound is fed in at least two input rates, so that the heat production of the reaction between 2-ethylhexanal and formaldehyde immediately after each increase of the feeding rate is almost the same.

4. The process according to claim 3, wherein the latter feeding rate of the hydroxide compound is about 10 to 80% higher than the former feeding rate.

5. The process according to claim 4, wherein the hydroxide compound is fed into the reaction mixture in at least three input rates.

6. The process according to claim 1, wherein the feed rate of the hydroxide compound is increased continuously.

7. The process according to claim 1, wherein the amount of hydroxide compound feed per unit time is increased to at least double during the reaction.

8. The process according to claim 1, wherein the molar ratio of the hydroxide compound feed and 2-ethylhexanal is greater than 1.

9. The process according to claim 1, wherein formaldehyde and the hydroxide compound are used in the form of concentrated solutions.

10. The process according to claim 9, wherein an aqueous solution of formaldehyde of 30 to 50 weight-%, is used, containing 2 to 20 weight-% lower alcohol, such as methanol.

11. The process according to claim 1, wherein the molar ratio of formaldehyde to 2-ethylhexanal is ca 2.1 to 5.

12. The process according to claim 1, wherein at least one member selected from the group consisting of sodium hydroxide, potassium hydroxide, lithium hydroxide, or earth-alkaline metal hydroxide is used as the hydroxide compound.

13. The process according to claim 1, wherein the reaction temperature is kept at 50 to 70° C. at least essentially during the reaction.

14. The process according to claim 1, wherein the reaction mixture, consisting of an organic and an aqueous phase, is neutralized after the reaction with strong mineral acid.

15. The process according to claim 14, wherein the aqueous phase is separated and the organic phase is washed with water, with a pH value >7.

16. The process according to claim 15, wherein the organic phase is washed with water having a pH value lower than 7.

17. The process according to claim 1, wherein the aqueous phase is separated after the reaction from the reaction mixture, which consists of an organic and an aqeous phase, and the aqeuous phase is neutralized with a strong mineral acid.

18. The process according to claim 17, wherein the organic phase is washed with water to remove the soluble salts.

19. The process according to claim 14, wherein the pH value of the organic phase is adjusted to about 6 to 7, and then the raw BEPD product thus obtained is subjected to distillation to recover the BEPD.

20. The process according to claim 3, wherein the latter feeding rate of the hydroxide compound is 20 to 60% higher than the former feeding rate.

21. The process according to claim 10, wherein the lower alcohol is methanol.

22. The process of claim 1, wherein the molar ratio of formaldehyde to 2-ethylhexanal is greater than 2.3.

23. The process according to claim 11, wherein the molar ratio is higher than 2.3.

* * * * *